(12) United States Patent
Volkwardt et al.

(10) Patent No.: US 9,867,535 B2
(45) Date of Patent: Jan. 16, 2018

(54) METHOD FOR THE RELIABLE DETERMINATION OF THE AXIAL LENGTH OF AN EYE

(71) Applicant: CARL ZEISS MEDITEC AG, Jena (DE)

(72) Inventors: Martin Volkwardt, Kröslin (DE); Ferid Bajramovic, Jena (DE); Tobias Bühren, Magdala (DE)

(73) Assignee: Carl Zeiss Meditec AG, Jena (DE)

( * ) Notice: Subject to any disclaimer, the term of this patent is extended or adjusted under 35 U.S.C. 154(b) by 53 days.

(21) Appl. No.: 14/431,206

(22) PCT Filed: Sep. 27, 2013

(86) PCT No.: PCT/EP2013/070196
§ 371 (c)(1),
(2) Date: Mar. 25, 2015

(87) PCT Pub. No.: WO2014/049122
PCT Pub. Date: Apr. 3, 2014

(65) Prior Publication Data
US 2015/0250384 A1    Sep. 10, 2015

(30) Foreign Application Priority Data

Sep. 28, 2012 (DE) .......................... 10 2012 019 473

(51) Int. Cl.
*G06T 7/00* (2017.01)
*A61B 3/10* (2006.01)

(52) U.S. Cl.
CPC ............ *A61B 3/1005* (2013.01); *A61B 3/102* (2013.01)

(58) Field of Classification Search
CPC ......... A61B 3/102; A61B 3/0025; A61B 3/10; A61B 3/1005; A61B 3/1015; A61B 3/113;
(Continued)

(56) References Cited

U.S. PATENT DOCUMENTS 5,321,501 A    6/1994 Swanson et al.
7,452,077 B2   11/2008 Meyer et al.
(Continued)

FOREIGN PATENT DOCUMENTS

DE    10 2010 051 281 A1    5/2012
DE    10 2012 016 379.7 A1   2/2014
EP          1 842 482 A2    10/2007

OTHER PUBLICATIONS

Notification of transmittal Translation of the International Preliminary Report on Patentability for International Application No. PCT/EP2013/070196, dated Apr. 9, 2015, 6 pages.
(Continued)

*Primary Examiner* — Bumsuk Won
*Assistant Examiner* — Henry Duong
(74) *Attorney, Agent, or Firm* — Patterson Thuente Pedersen, P.A.

(57) ABSTRACT

A method for determining the axial length of an eye by optical coherence tomography (OCT), in which the alignment of the measuring instrument to the eye is monitored to enable reliable determination of the axial length of the eye. B-scans are carried out following alignment from which scans of the retinal tissue structures are detected to determine the axial lengths, which are then used in the detection of the fovea in order to monitor alignment. The axial lengths determined from the B-scans are then confirmed or corrected and output depending, on the determined position of the fovea or the lateral distance thereof from the optical axis of
(Continued)

the measuring instrument. The method is particularly suitable for OCT methods in which the axial length is determined on the basis of an A-scan along the axial dimension of the eye.

16 Claims, 1 Drawing Sheet

(58) Field of Classification Search
CPC ....... A61B 3/12; A61B 3/1225; A61B 5/1072; A61B 3/032; A61B 3/103; A61B 3/107; G06T 7/00; G06T 7/0002; G06T 7/0012; G06T 7/0014; G06T 7/0083
USPC ........ 351/200, 246, 205, 206, 208, 209, 210
See application file for complete search history.

(56) References Cited

U.S. PATENT DOCUMENTS

| | | | |
|---|---|---|---|
| 2008/0079898 A1* | 4/2008 | Miwa | A61B 3/1005 351/205 |
| 2008/0100612 A1* | 5/2008 | Dastmalchi | G06F 19/321 345/418 |
| 2009/0163898 A1 | 6/2009 | Gertner et al. | |
| 2011/0034803 A1* | 2/2011 | Stetson | G06T 15/08 600/425 |
| 2011/0069279 A1 | 3/2011 | Hacker et al. | |
| 2011/0299034 A1 | 12/2011 | Walsh et al. | |
| 2012/0150029 A1 | 6/2012 | Debuc | |

OTHER PUBLICATIONS

PCT International Search Report with English translation PCT/EP2013/070196, dated Jan. 8, 2014, 5 pgs.

DE Search Report with English translation for DE 10 2012 019 473.0, dated Mar. 21, 2014, 10 pages.

ISO/CD 19980, "Ophthalmic instruments—Corneal topographers." 2009, 31 pages.

Wolfgang Haigis, "Optical Coherence Biometry," Modern Cataract Surgery, T. Kohnen, Ed. Basle: Karger Publishers, 2002, vol. 34, pp. 119-130.

Haag-Streit International, Haig-Streit AG, Koeniz, Switzerland, "Biometry Connected . . . " Jun. 2010, 3 pages.

D. C. Fernandez, "Delineating Fluid-Filled Region Boundaries in Optical Coherence Tomography Images of the Retina," IEEE Trans. Med. Imaging, vol. 24. No. 8, pp. 929-945, Aug. 2005.

* cited by examiner

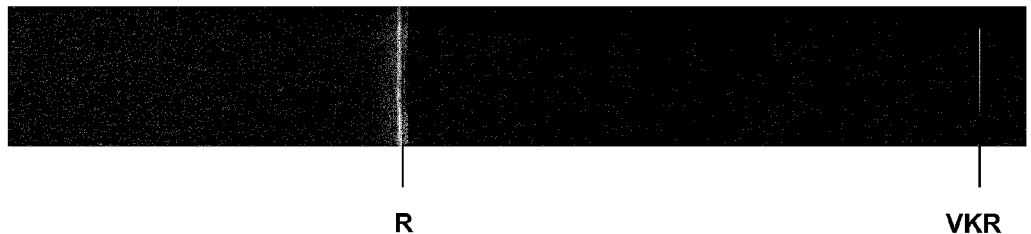
R    VKR
Figure 1
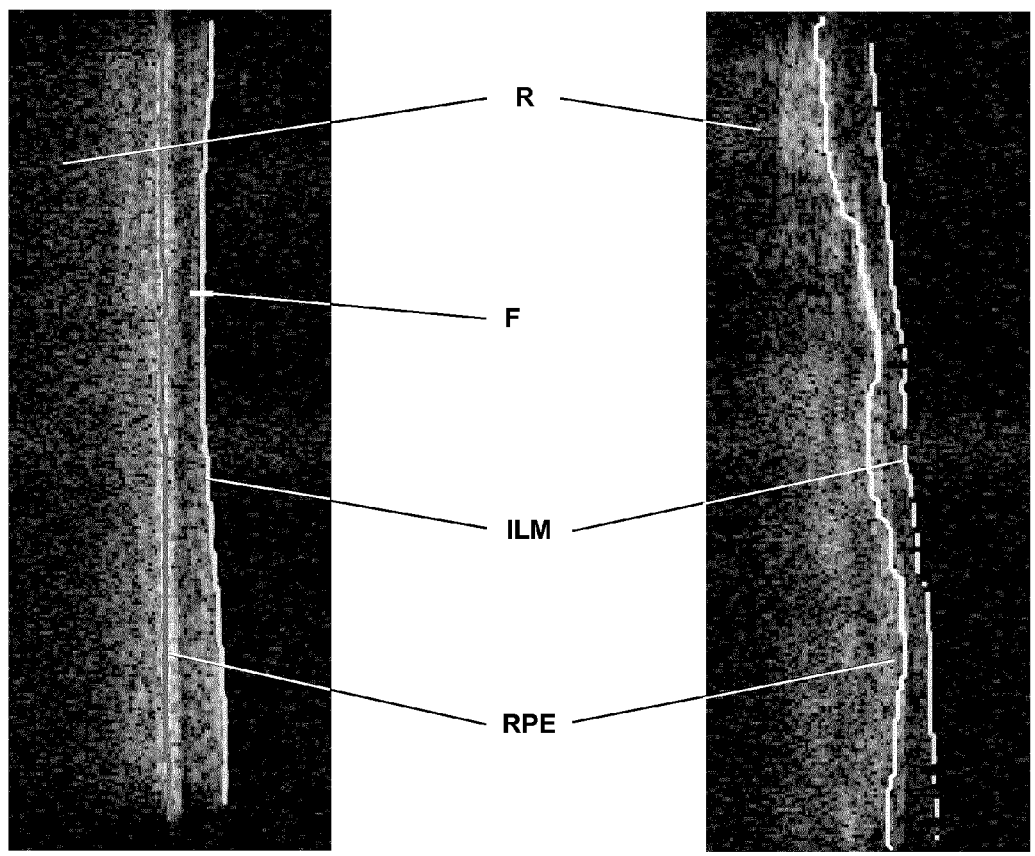
Figure 2
Figure 3

METHOD FOR THE RELIABLE DETERMINATION OF THE AXIAL LENGTH OF AN EYE

RELATED APPLICATIONS

The present application is a National Phase entry of PCT Application No. PCT/EP2013/070196, filed Sep. 27, 2013, which claims priority from DE Patent Application No. 10 2012 019 473.0, filed Sep. 28, 2012, said applications being hereby incorporated by reference herein in their entirety.

FIELD OF THE INVENTION

The present invention relates to a method for determining the axial length of an eye by means of optical coherence tomography (OCT), in which the alignment of the measuring instrument with the eye is monitored for all one-dimensional or two-dimensional scans in order to be able to guarantee a reliable determination of the axial length of the eye.

BACKGROUND

The preoperative selection of intraocular lenses in the treatment of cataracts constitutes an important application. The most significant measured value is the axial length of the eye from the front of the cornea to the retina. According to the prior art, this is often measured contactlessly by optical interferometric methods, which are known under the name of PCI (partial coherence interferometry) or OCT (optical coherence tomography). In these methods structural transitions are illustrated as one-dimensional depth profiles (A-scan), as two-dimensional depth cut images (B-scan) or three-dimensional tomograms, wherein specular reflections on the optical interfaces, and/or light which is scattered in the different media of the eye, are detected.

In both measuring methods it is important that the measurement takes place along an axially oriented axis which corresponds to the visual axis. Otherwise errors can occur during the selection of the IOL which lead to a considerable defective vision of the patient after the implantation of the IOL.

In order to ensure the measurement along the visual axis with great reliability, during the measurement according to the prior art using the optical measuring instrument the patient is provided with a fixation light onto which the patient fixates his eye. In this way the visual axis of the eye is aligned with the main measuring axis of the device which simultaneously corresponds to the Z axis of the coordinate system of the measuring instrument. This can be seen from the literature [1]. If the device axis is aligned with the visual axis, the cornea and the retina are in most cases positioned sufficiently perpendicular to the main measuring axis, so that the measuring beams reflected from the cornea and the retina can be easily detected by the measuring instrument.

According to a first method described in the literature [2], the measurement of the axial length takes place by application of partial coherence interferometry in the double-beam method. In this case two beams with different optical path lengths impinge on the eye and are specularly reflected on the front of the cornea and the retina, resulting in interference. The signals at different optical path lengths are indicative of the eye length. Since a usable signal is only generated when a specular reflection from both the cornea and the retina is present, this method offers the advantage that for generation of a distance signal the cornea and the retina are approximately perpendicular to the measuring beam and thus to the device axis.

It has been shown experimentally that under these measurement conditions, which lead to a usable distance signal, in good approximation the device axis/measuring axis is identical to the visual axis, and the distance measured along the device axis corresponds to the axial length which is determinative for calculating the IOL.

Thus this measurement method virtually ensures that, in the case of excessively great deviations of the visual axis from the device axis, no incorrect measured value for the eye length is obtained and used for calculating the IOL.

However, it is a disadvantage that for the duration of the measurement time the patient must give a minimum amount of cooperation for the fixation. If this is not the case, no or very few, and thus statistically hardly reliable, measurements can be determined for the axial eye lengths.

It is a further disadvantage that measured values for B-scans or the measurement of the anterior chamber depth are difficult to realize. This is because during such measurements the tilted position of the measuring beam with respect to the boundary layers of either the cornea or the lens the boundary layers show no specular reflection which can also be detected by the device. Thus, newer methods which promise increased reliability in the selection of the intraocular lenses and require the measurement of the anterior chamber depth, lens thickness, or lens radii are not possible or only possible with difficulty.

According to a second method described in the literature [3], the measurement of intraocular distances takes place with the aid of one or more so-called B-scans which are obtained by means of optical coherence tomography. Thus the front face of the cornea and the retina as well as further tissue structures can be resolved. For example, cornea thickness, anterior chamber depth, and/or lens thickness can be determined.

The basic principle of the OCT method described for example in U.S. Pat. No. 5,321,501 A is based on white light interferometry and compares the propagation time of a signal with the aid of an interferometer (generally a Michelson or Mach-Zehnder interferometer). The arm with a known optical path length is used as a reference external to the object for the measurement arm. The interference of the signals from both arms produces a pattern from which the relative optical path length within an A-scan (single depth signal) can be read out. In the one-dimensional scanning grid methods the beam is then guided transversely in one or two directions, so that a two-dimensional B-scan or a three-dimensional tomogram can be recorded. Even in the B-scan this produces sufficient signals because with this method both specular reflections and also scattering in the object are detected.

However, in contrast to the double-beam method, in such methods it is not ensured by the measurement principle itself that the axis length (the axial length of the eye), which is important for calculating the intraocular lenses, is measured along the correct axis (the visual axis). This is because a recording and a signal are possible even if the measuring beam does not impinge perpendicularly on the front face of the cornea and/or is not aligned along the visual axis. The measurement along the device axis then supplies an A-scan which, considered alone, shows no discernible defect, even if it is not measured along the visual axis due to lack of fixation. However, reading off the axis length from the measurement along the device axis would generally lead to incorrect and systematically shortened measurement values, since in the event of lack of alignment of the measuring instrument with the visual axis, because of eye movement and/or lack of fixation, the A-scan measures laterally too far off the visual axis, which in a typically convex eye leads to a shortening of the cornea-retina distance.

With these B-scans the problem generally arises of the lateral attribution of the B-scans in terms of the eye. In this case, because of inaccurate alignment, eye movements not only during the measurement but also during the alignment of the measurement device with the eye lead to defective measurements.

If such eye movement is not taken into consideration, a B-scan and the intraocular distances which can be evaluated in such a B-scan are laterally offset in terms of the eye and thus incorrectly attributed. As a result it is not ensured that the A-scan along the device axis and/or the A-scan within a B-scan which runs along the device axis actually measures the eye length. Moreover, even with exact alignment, only a few A-scans—namely only those along the device axis—can be used for calculating the axial length, so that the measured axial length is encumbered by a relatively high statistical uncertainty.

A further method for determination of the distances between localized interfaces in the eye is already known from DE 10 2010 051 281 A1. With the aid of the scans which are recorded under different conditions and include at least two of the interfaces present in the eye, a parametric eye model can be appropriately adapted by a control and evaluation unit so that model-based determination of the eye biometrics can take place.

However, even with this solution it is problematic that the automatic evaluation of A-scans and B-scans to obtain biometric data is subject to a plurality of measuring situations and disruptions. These include, for example, attenuation of the measuring beam in the case of cataracts or defocusing of the measuring beam in the event of refractive errors or also the presence of pathological conditions.

In the as yet unpublished DE 10 2012 016 379.7 a method for measuring the axial length of an eye by means of OCT is described, wherein the alignment of the measuring instrument with the eye is monitored during the measurement. For this purpose the A-scans of the OCT with respect to the topography of the cornea are registered and the axial length of the eye is determined from the A-scan which is located at least approximately on the visual axis. Although in this way a reliable determination of the axial length is ensured, this always necessitates the topography of the cornea which is either already present or must first be measured.

A further solution which monitors and/or corrects the alignment of a measuring instrument with an eye is described for example in U.S. Pat. No. 7,452,077 B2. In this case the pattern of crossed B-scans is used to improve the misalignment, as the offset for each pair of B-scans relative to the vertex of the cornea is determined and if necessary corrected. It is a disadvantage here that the position of the visual axis on the cornea is not generally known.

BIBLIOGRAPHY

[1] ISO/CD 19980, "Ophthalmic instruments—Corneal topographers." 2009
[2] W. Haig is, "Optical Coherence Biometry," in Modern Cataract Surgery, T. Kohnen, Ed. Basle: Karger Publishers, 2002, pp. 119-130
[3] Haag-Streit A G, "Biometry Connected . . . " June 2010
[4] D. C. Fernandez, "Delineating Fluid-Filled Region Boundaries in Optical Coherence Tomography Images of the Retina," IEEE Trans. Med. Imaging, vol. 24. No. 8, pp. 929-945, 2005.

SUMMARY OF THE INVENTION

The object of the present invention is to develop a method for reliable determination of the axial length of an eye which eliminates the disadvantages of the solutions known from the prior art known and ensures that only the measured values which were recorded with the most exact alignment possible of the main measuring axis of the measuring instrument with the visual axis of the eye of the patient are used for determination of the axial length.

The object is achieved by the method according to the invention for reliable determination of the axial length of an eye by means of optical coherence tomography (OCT), wherein the eye is aligned with a fixation mark so that the main measuring axis of the measuring instrument coincides at least approximately with the visual axis of the eye, according to the method steps:
  a) the B-scans are performed,
  b) the retinal tissue structure detected from the B-scans using one or different criteria are segmented and
  c) when possible the axial lengths are determined from the B-scans,
characterized in that the segmentations of the retinal tissue structure carried out in the method step b) using different criteria are used for detection of the fovea in order to monitor the alignment of the optical axis of the measuring instrument with the visual axis of the eye, and the axial lengths determined from the B-scans are confirmed or corrected and output depending on the determined position of the fovea or the lateral distance thereof from the optical axis of the measuring instrument. If the position of the fovea could not be determined, a warning message points out the restricted reliability of the axial length measurement and possible pathological changes.

The method is particularly suitable for OCT methods in which the axial length is determined on the basis of an A-scan along the axial dimension of the eye, wherein an individual A-scan detects the entire length of the eye from the cornea to the retina.

The present invention relates to a method for determining the axial length of an eye, which may be used in particular in biometric instruments in ophthalmology. In this case the axial length of the eye from the front of the cornea to the retina constitutes the most important measured value for the preoperative selection of intraocular lenses in the treatment of cataracts.

The possibility in some circumstances of obtaining indications of pathological changes to the retina during the determination of the axial length of an eye is completely novel for biometric measuring instruments and allows a much broader application. The indications of pathological changes to the retina mostly involve no additional expenditure for doctors or operators in the context of the preparation for a cataract operation, and in the case of such an indication a more precise investigation, for example with additional diagnostic methods and instruments, is recommended.

BRIEF DESCRIPTION OF THE DRAWINGS

The invention is described in greater detail below with reference to embodiments. In the drawings:

FIG. 1 shows a B-scan that starts from the vertex/cornea reflection and extends to the retinal tissue structures, FIG. 2 shows retinal tissue structures of a healthy eye as a detail of a B-scan, and FIG. 3 shows retinal tissue structures of an eye with pathological changes as a detail of a B-scan.

DETAILED DESCRIPTION

In the proposed method for reliable determination of the axial length of an eye by means of optical coherence tomography (OCT), wherein the eye is aligned with a fixation mark so that the main measuring axis of the measuring instrument coincides at least approximately with the visual axis of the eye, according to the following method steps:
  a) the B-scans are performed,
  b) the retinal tissue structure detected from the B-scans using one or different criteria are segmented, and
  c) when possible the axial lengths are determined from the B-scans.

According to the invention the segmentation of the retinal tissue structures carried out in the method step b) using one or different criteria are used for detection of the fovea in order to monitor the alignment of the optical axis of the measuring instrument with the visual axis of the eye, wherein
  d) in the event that the determined position of the fovea lies on the optical axis of the measuring instrument, the axial lengths categorized as correct are aggregated and the method is ended with the output of the resulting axial length,
  e) in the event that the position of the fovea has been determined but this position does not lie on the optical axis of the measuring instrument, the lateral distance between the two is determined, in the case of a small lateral distance the axial length of the A-scans at the determined position is categorized as correct, aggregated and output, or if the lateral distance is too large the method is ended, for example without output of a resulting axial length but a corresponding indication of an insufficient alignment of the optical axis of the measuring instrument with the visual axis of the eye, and
  f) in the event that the position of the fovea could not be determined, a corresponding warning message points out the restricted reliability of the axial length measurement and possible pathological changes.

Before the determination of the axial lengths of the eye it is necessary according to the invention to segment the retinal tissue structures recorded in the B-scans, i.e. to identify the different tissue structures in the B-scan. In this case for OCT-based methods the segmentation of the so-called "retinal pigment epithelium" (abbreviated to RPE) is of particular interest, since the light beams of the scanning illumination are scattered on this layer of the retinal tissue structure.

For the subsequent detection of the fovea, in order to monitor the alignment of the optical axis of the measuring instrument with the visual axis of the eye further segmentations of the retinal tissue structure are carried out using different criteria. In addition to the already mentioned retinal pigment epithelium (RPE) the so-called interior limiting membrane (ILM) is of interest here. Due to corresponding specifications for the segmentation of the measurement signals, both the ILM and also the RPE can be resolved and detected by OCT-based measuring methods.

For the segmentation or these segmentations, in particular the location of the RPE and/or the ILM, a B-scan can be analyzed with regard to different criteria. These are gradient strength, intensity, signal-to-noise ratio or local entropy. For the segmentation of an individual tissue structure individual criteria or also combinations thereof are used.

An exact alignment of the optical axis of the measuring instrument with the visual axis of the eye is indispensable for reliable determination of the axial length of the eye. For the measurements along the visual axis a good fixation of the patient as well as the correct alignment of the biometric measuring instrument with the eye are necessary. Under these conditions it is to be expected that the fovea is located on the main measuring axis of the measuring instrument. In order to be able to monitor the alignment, according to the invention the retinal tissue structures are recorded with the B-scan. With the aid of optical coherence tomography (OCT) the measurement of the axial length of an eye is only possible if a sufficiently great scanning depth can be achieved. In this connection FIG. 1 shows a B-scan which starts from the vertex/cornea reflection and extends to the retinal tissue structures R.

A correct axial length can generally be measured only along the visual axis which inevitably extends through the center of the sharpest vision, which is to say through the fovea. The position of the fovea detected in the B-scan can therefore be compared with the position of the main measuring axis in order to check whether the conditions for a correct measurement of the axial length are met.

According to the invention the aforementioned segmentations of the retinal tissue structures are of interest, since these are used for detection of the fovea.

The fovea of an anatomically healthy eye is for example characterized by the following features:
  the fovea is located at the lowest point of the ILM,
  the fovea is located at the minimum distance between RPE and ILM,
  the fovea exhibits the minimum scattering and reflection of light and thus the minimum signal intensity in the region between RPE and ILM.

In this case the minimum signal intensity can be determined in the region between RPE and ILM, and the intensities between the segmentations of ILM and RPE or a part thereof are added up for each A-scan. The minimum intensity sum then defines the position of the fovea.

Due to the corresponding evaluation of the retinal pigment epithelium (RPE) and/or the interior limiting membrane (ILM) the fovea can be detected in a simple manner. Presupposing that the B-scans encompass the fovea, the position thereof (at least in healthy eyes) can be determined automatically.

In an embodiment of the method one or more of said features can be used for the determination of the position of the fovea, wherein the arithmetic mean value is determined from the individually determined positions after the removal of rogue results.

The method according to the invention is characterized in that the segmentation of the retinal tissue structures carried out in the method step b) using one or different criteria is used for detection of the fovea in order to monitor the alignment of the optical axis of the measuring instrument with the visual axis of the eye, wherein
  d) in the event that the determined position of the fovea lies on the optical axis of the measuring instrument, the axial lengths categorized as correct are aggregated and the method is ended with the output of the resulting axial length, e) in the event that the position of the fovea has been determined but this position does not lie on the optical axis of the measuring instrument, the lateral distance between the two is determined, in the case of a small lateral distance the axial length of the A-scans at the determined position is categorized as correct, aggregated and output, or if the lateral distance is too large the method is ended, for example without output of a resulting axial length but a corresponding indication of an insufficient alignment of the optical axis of the measuring instrument with the visual axis of the eye, and f) in the event that the position of the fovea could not be determined, a corresponding warning message points out the restricted reliability of the axial length measurement and possible pathological changes.

After the segmentations of the retinal tissue structure has been carried out the position of the fovea must be detected. As a function of the determined position of the fovea, three cases are distinguished to which reference is made in greater detail below.

In the first case, for which according to the method step d) the determined position of the fovea lies on the optical axis of the measuring instrument, the axial lengths categorized as correct are aggregated and the method is ended with the output of the resulting axial length. Since the measured axial length is regarded as reliable, no further measures need to be taken and the method can be ended.

According to the invention the axial lengths categorized as correct are aggregated after detection of rogue results. In this case the detection of rogue results takes place in such a way that, starting from the median of the axial length measurements, a range for the axial lengths to be expected is defined and measured values outside this range are categorized as rogue results and are not allowed for an aggregation.

In this case the axial lengths categorized as correct are aggregated, and the arithmetic mean value is formed from the axial lengths remaining after the detection of rogue results, wherein this can only take place if a sufficiently large number, for example at least 2 axial lengths remain.

In this case FIG. 2 shows retinal tissue structures of a healthy eye as a detail of a B-scan. The illustration includes, in addition to the retinal tissue structures R, the segmentations of the RPE and the ILM, as well as the determined position of the fovea F. Since in this case the retinal tissue structures are well resolved and both the RPE and also the ILM are segmented exactly, the position of the fovea F can be determined without problems. As expected, the RPE appears just in a small region around the fovea.

In the second case, for which according to the method step e) the position of the fovea was determined but this position does not lie on the optical axis of the measuring instrument, the lateral distance between the two is determined, with a small lateral distance the axial length of the A-scans at the determined position is categorized as correct, aggregated and output or when the lateral distance is too large the method is ended for example without output of a resulting axial length but a corresponding indication of an insufficient alignment of the optical axis of the measuring instrument with the visual axis of the eye.

The reason why the determined position of the fovea is not located on the optical axis of the measuring instrument should be sought in an insufficient fixation of the patient and/or an inaccurate alignment of the measuring instrument with the visual axis of the eye. Whereas in the case of a small lateral distance the axial length of the A-scan at the determined position can be categorized as correct, aggregated and output, in the case of a large lateral distance this is no longer practical.

Since the lateral distance of the determined position of the fovea from the optical axis of the measuring instrument gives an indication of the fixation or alignment of the measuring instrument, this can be used advantageously as fixation control for the measurement and for verification of the measured axial length.

The extent to which the lateral distance of the determined position of the fovea from the optical axis of the measuring instrument may be regarded as small should be decided from case to case. Up to an acceptance threshold which is to be defined, the determined position of the fovea is categorized as correct and the axial lengths of the relevant A-scans are aggregated and output. Thus no changes to the measurement conditions are required, so that the measurements of the axial lengths take place furthermore along the main measuring axis.

If the lateral distance of the determined position of the fovea with respect to the optical axis of the measuring instrument is too great, i.e. is it is located outside the defined acceptance threshold, then the method is interrupted without output of a resulting axial length or is started again. In each case, however, a corresponding indication of an insufficient alignment of the optical axis of the measuring instrument with the visual axis of the eye is given.

However, it is also possible in this case that the measurements of the axial lengths take place at the location of the detected fovea position.

In the third case for which according to the method step f) the position of the fovea could not be determined, a corresponding warning message points out the restricted reliability of the axial length measurement and possible pathological changes.

The reason why the determined position of the fovea cannot be determined should be sought either in an insufficient fixation of the patient and/or an inaccurate alignment of the measuring instrument with the visual axis of the eye or the presence of pathological changes to the eye.

If the cause is merely an insufficient fixation of the patient and/or an inaccurate alignment of the measuring instrument, then this can generally be remedied by a new measurement. Here too the method steps a) to c) and also the detection of the position of the fovea should be carried out again.

However, if even after new measurements the position of the fovea cannot be determined, then the cause actually appears to lie in the presence of pathological changes to the eye. In this case the pathological changes can affect both the retina and also the lens and cornea. The following changes may be mentioned here by way of example: macular degeneration, detachment of the retina, cataract or a cloudy cornea.

Pathological changes can change and/or attenuate the scan signals, in particular of the retinal tissue structures, so that detection is difficult or even impossible. Thus a segmentation of the ILMs and the location of the fovea are likewise no longer possible.

In addition to a reliable axial length measurement the segmentations of RPE and ILM also give indications of pathological changes to the eye which in turn can have a considerable influence on a reliable axial length measurement.

Since, as already mentioned, the RPE should appear just in a small region around the fovea, a form which deviates significantly from a straight line may be an indication that an insufficient fixation of the patient, an inaccurate alignment of the measuring instrument or pathological changes are present.

In this connection FIG. 3 shows retinal tissue structures of an eye with pathological changes as a detail of a B-scan. The illustration includes, in addition to the retinal tissue structures R, the segmentations of the RPE and the ILM. Although both the RPE and also the ILM could be segmented, the position of the fovea F could not be determined.

Whereas the segmentation of the ILM still has an approximately "normal" progression, the segmentation of the RPE exhibits considerable fluctuations, which do not correspond to the expected shape of a healthy retina and indicate potential pathological changes.

However, it has also been shown that in principle the axial length can nevertheless be measured so long as the signals of the retinal tissue structures can be detected from the B-scans and the RPE can be segmented.

Since the automatic location of the fovea cannot be carried out correctly or even at all in many cases, above all in the case of pathological changes, additional measures may be sensible.

On the one hand the segmented RPE and/or ILM can be subjected to a plausibility check in order to evaluate the reliability of the determined position of the fovea and of the axial length measurement.

In this case the plausibility check may be based on the criteria used for the segmentation, such as gradient strength or intensity, or on features such as signal-to-noise ratio or local entropy.

Non-plausible segmentations may indicate pathological changes, so that the measured axial length and the determined fovea position are regarded as not reliable. In this case a warning message is displayed to the user. Possible options which are available are for example simultaneously presented or predetermined for the user.

On the other hand the operator may be offered the possibility of manually marking the position of the fovea in the OCT recording, for which an input device, such as for example a mouse, a touch screen or the like must be available.

In particular if a pathological change is suspected, but also independently thereof, it has proved expedient to determine a thickness profile of the layer between RPE and ILM as a plausibility criterion and to compare it with that of one or more healthy eyes or a model eye. Furthermore, the presence of a pathological change can be confirmed by comparison of the intensity distribution of the retinal tissue structures or the three-dimensional appearance thereof.

However, characteristics of the retina signal, such as for example intensity distribution, structure, etc. can also be evaluated as plausibility criterion. A similar use of the characteristics of the retina signal is known according to the article [4] by D. C. Fernandez for diagnosis of the retina.

With the solution according to the invention a method is provided for determining the axial length of an eye by means of optical coherence tomography, which ensures a reliable determination of the axial length of the eye. The disadvantages of the solutions known from the prior art are eliminated and it is ensured that only the measured values which were recorded with the most exact alignment possible of the optical axis of the measuring instrument with the visual axis of the eye of the patient are used for determination of the axial length.

The possibility in some circumstances of obtaining indications of pathological changes to the eye during the determination of the axial length of an eye, is completely novel for biometric measuring instruments and allows a much broader application. The indications of possible pathological changes to the retina mostly involve no additional expenditure for doctors or operators in the context of the preparation for a cataract operation, and in the case of such an indication a more precise investigation, for example with special diagnostic methods and instruments, is recommended.

It has been shown that the monitoring of the alignment of the optical axis of the measuring instruments with the visual axis of the eye, even in the event of insufficient fixation and/or inaccurate alignment of the measuring instrument, enables a reliable determination of axial lengths, wherein the determination of the position of the fovea can improve or at least verify the measurement results.

In addition automatic indications of unusual structures can be made, which indicate pathological changes and moreover can influence the measurement of the axial length and can call into question the reliability thereof.

Whereas the above embodiments emphasize the checking of the fixation in the case of axial length measurement with reference to the location of the fovea in the OCT signals, however, the basic idea of checking the location of the fovea by the OCT in instruments which integrate or combine different measuring modalities can also be used advantageously for monitoring fixation in the measurement of the other modalities.

Thus, for example, in the measurements for topography in a combined instrument consisting of a Placido topograph and an OCT which images the retina, the fixation in the case of the Placido topography measurements with reference to the location of the fovea can take place in the OCT measurements. In this case the OCT measurements are ideally carried out virtually simultaneously with the topography measurements. Thus topography measurements which take place when there is a lack of fixation can be recognized in the OCT by excessive deviation of the fovea position from the instrument axis and can be ruled out by further evaluation or diagnostic use.

The invention claimed is:

1. A method for reliable determination of an axial length of an eye by application of optical coherence tomography (OCT), wherein the eye is aligned with a fixation mark so that the main measuring axis of the measuring instrument coincides at least approximately with the visual axis of the eye;

the method comprising:
 a) performing B-scans;
 b) segmenting retinal tissue structure detected from the B-scans using one or different criteria; and
 c) when possible, determining the axial lengths from the B-scans;
 wherein segmentation of the retinal tissue structures carried out in method step b) using one or different criteria is used for detection of a position of a fovea to monitor alignment of an optical axis of the measuring instrument with the visual axis of the eye;
 d) in an event that the position of the fovea lies on the optical axis of the measuring instrument, aggregating the axial lengths categorized as correct dependent upon a determined position of the fovea or the lateral distance of the fovea from the optical axis of the measuring instrument and ending the method and outputting a resulting axial length,
 e) in an event that the position of the fovea has been determined but the position does not lie on the optical axis of the measuring instrument, determining the lateral distance between the fovea and the optical axis of the measuring instrument, in the case of a lateral distance within a measurement threshold measured from a visual axis of the eye, aggregating the axial length of the A-scans at the determined position categorized as correct dependent upon the determined position of the fovea or the lateral distance of the fovea from the optical axis of the measuring instrument, and outputting the axial length, or if the lateral distance exceeds the measurement threshold ending the method; and f) in an event that the position of the fovea could not be determined, presenting a corresponding warning message pointing out the restricted reliability of the axial length measurement and possible pathological changes of tissues of the eye including changes to the retina, lens or cornea.

2. The method according to claim 1, further comprising, if the lateral distance exceeds the measurement threshold, ending the method without output of a resulting axial length and presenting a corresponding indication of an insufficient alignment of the optical axis of the measuring instrument with the visual axis of the eye.

3. The method according to claim 1, wherein according to method step b) the retinal pigment epithelium (RPE) and the interior limiting membrane (ILM) are segmented out of the retinal tissue structure using different criteria.

4. The method according to claim 3, wherein according to a first feature the fovea is identified by the lowest point of the ILM.

5. The method according to claim 4,
wherein according to a first feature the fovea is identified by the lowest point of the ILM;
wherein according to a second feature the fovea is identified by the smallest distance between the RPE and the ILM
wherein according to a third feature the fovea is identified by the smallest scattering and reflection of light and thus by the lowest signal intensity between the RPE and the ILM
wherein more than one feature is used for determination of the position of the fovea; and
further wherein the determined positions are averaged arithmetically after the removal of rogue results.

6. The method according to claim 5, further comprising starting from the median of the axial length measurements defining a range for the axial lengths to be expected and categorizing measured values outside this range as rogue results that are not allowed for an aggregation.

7. The method according to claim 3, wherein according to a second feature the fovea is identified by the smallest distance between the RPE and the ILM.

8. The method according to claim 3, wherein according to a third feature the fovea is identified by the smallest scattering and reflection of light and thus by the lowest signal intensity between the RPE and the ILM.

9. The method according to claim 3, further comprising subjecting the segmented RPE and/or ILM to a plausibility check.

10. The method according to claim 9, wherein the plausibility check is initiated if the position of the fovea cannot be determined.

11. The method according to claim 9, wherein the plausibility check is based on the criteria used for the segmentation.

12. The method according to claim 11, wherein the criteria used for the segmentation are selected from a group consisting of gradient strength and intensity.

13. The method according to claim 9, wherein the plausibility check is based on features selected from a group consisting of signal-to-noise ratio and local entropy.

14. The method according to claim 9, further comprising determining a thickness profile of a layer between the RPE and the ILM as a plausibility criterion and comparing the thickness profile with that of one or more healthy eyes or a model eye.

15. The method according to claim 1, further comprising aggregating the axial lengths determined from the B-scans, and determining an arithmetic mean value from the axial lengths remaining after the detection of rogue results, wherein aggregating the axial lengths determined from the B-scans, and determining an arithmetic mean value from the axial lengths remaining after the detection of rogue results can only take place if at least two axial lengths remain.

16. The method according to claim 1, wherein the sufficiently large number is at least 2 remaining axial lengths.

* * * * *

UNITED STATES PATENT AND TRADEMARK OFFICE
CERTIFICATE OF CORRECTION

PATENT NO. : 9,867,535 B2  
APPLICATION NO. : 14/431206  
DATED : January 16, 2018  
INVENTOR(S) : Martin Volkwardt et al.

Page 1 of 1

It is certified that error appears in the above-identified patent and that said Letters Patent is hereby corrected as shown below:

On the Title Page

Under (56) OTHER PUBLICATIONS, Line 1, delete "transmittal" and insert --transmittal of Copies of--

Under (57) ABSTRACT, Line 5, delete "alignment" and insert --alignment,--

Under (57) ABSTRACT, Line 10, delete "depending," and insert --depending--

On page 2, Under (56) OTHER PUBLICATIONS, delete "Haig-Streit" and insert --Haag-Streit--

In the Specification

Column 3, Line 67, delete "A G," and insert --AG,--

Column 4, Line 25, delete "segmented and" and insert --segmented, and--

Column 5, Line 63, delete "interior" and insert --internal--

Column 6, Line 47, delete "interior" and insert --internal--

Column 10, Line 29, delete "topograph" and insert --topographer--

Signed and Sealed this  
Seventh Day of April, 2020

Andrei Iancu  
*Director of the United States Patent and Trademark Office*